US012742785B2

(12) United States Patent
Jordan et al.

(10) Patent No.: US 12,742,785 B2

(45) Date of Patent: Sep. 22, 2026

(54) HIGH IONIC STRENGTH DISSOCIATION ASSAY FOR HIGH DRUG TOLERANT TESTING

(71) Applicant: Hoffmann-La Roche Inc., Little Falls, NJ (US)

(72) Inventors: Gregor Jordan, Gröbenzell (DE); Roland Staack, Munich (DE)

(73) Assignee: Hoffmann-La Roche Inc., Branchburg, NJ (US)

(*) Notice: Subject to any disclaimer, the term of this patent is extended or adjusted under 35 U.S.C. 154(b) by 876 days.

(21) Appl. No.: 17/982,361

(22) Filed: Nov. 7, 2022

(65) Prior Publication Data

US 2023/0063268 A1 Mar. 2, 2023

Related U.S. Application Data

(63) Continuation of application No. PCT/EP2021/061929, filed on May 6, 2021.

(30) Foreign Application Priority Data

May 8, 2020 (EP) .................................... 20173599

(51) Int. Cl.
*G01N 33/536* (2006.01)
*G01N 33/68* (2006.01)

(52) U.S. Cl.
CPC ....... *G01N 33/6854* (2013.01); *G01N 33/536* (2013.01)

(58) Field of Classification Search
CPC ......................... G01N 33/536; G01N 33/6854
See application file for complete search history.

(56) References Cited

U.S. PATENT DOCUMENTS

2020/0300852 A1* 9/2020 Dahl ...................... G01N 33/53

FOREIGN PATENT DOCUMENTS

WO 2008/033073 A1 3/2008
WO 2019/105916 A1 6/2019

OTHER PUBLICATIONS

Barbosa, M., et al., "Altering drug tolerance of surface plasmon resonance assays for the detection of anti-drug antibodies" Anal Chem (Epub: Jul. 22, 2013), 441(2):174-179 (Oct. 15, 2013).

Bourdage, J., et al., "An Affinity Capture Elution (ACE) assay for detection of anti-drug antibody to monoclonal antibody therapeutics in the presence of high levels of drug" J Immunol Methods 327(1-2):10-17 (Oct. 1, 2007).

Brady, A.M., et al., "Description of a novel multiplex avidity assay for evaluating HPV antibodies" J Immunol Methods 447:31-36 (Aug. 1, 2017).

(Continued)

*Primary Examiner* — Gailene Gabel

(74) *Attorney, Agent, or Firm* — Roberto K. Rodriguez

(57) ABSTRACT

Herein is reported a method for the determination of the presence of anti-drug antibodies in a sample comprising the steps of incubating the sample with $MgCl_2$ at a final concentration in the range of 1 N to 12 N; adding a tracer antibody and incubating the sample thereafter; incubating the isolated tracer antibody-anti-drug antibody-complexes with a detection antibody conjugated to a detectable label and determining the presence of anti-drug antibodies if a signal above a threshold level is obtained.

14 Claims, 6 Drawing Sheets

(56) References Cited

OTHER PUBLICATIONS

Butterfield, A., et al., "Comparison of assay formats for drug-tolerant immunogenicity testing" Bioanalysis 2(12):1961-1969 (Nov. 26, 2010).
Dandliker, W.B., et al., "The Effect of Chaotropic Ions on the Dissociation of Antigen-Antibody Complexes" ACS Biochemistry 6(5):1460-1467 (May 1, 1967).
Durkee, K., et al., "Immunoaffinity Chromatographic Purification of Russell's Viper Venom Factor Activator Using Elution in High Concentrations of Magnesium Chloride" Protein Expr Purif 4(5):405-411 (Oct. 1, 1993).
European Medicines Agency [EMA] et al., "Guideline on Bioanalytical Method Validation" (EMEA/CHMP/EWP/192217/2009; Rev. 1, Corr.2),:1-23 (Jul. 21, 2011).
European Medicines Agency [EMA] et al., "ICH M10 on Bioanalytical Method Validation—Scientific Guideline" (Reference No. EMA/CHMP/ICH/172948/2019),:1-45 (Jul. 27, 2022).
Heinrich, J., et al., "Proposal for a harmonized descriptive analyte nomenclature for quantitative large-molecule bioanalysis" Bioanalysis 7(24):3057-3062 (Oct. 27, 2015).
Hogben, D.N., et al., "HBsAg: anti-HBs immune complexes. A method for separating the constituent components and assessment of the affinity of the antibody" J Immunol Methods 93(1):29-36 (Oct. 23, 1986).
"International Preliminary Report on Patentability—PCT/EP2021/0619291/" (Report Issuance Date: Nov. 8, 2022; Chapter I), :pp. 1-9 (Nov. 17, 2022).
"International Search Report—PCT/EP2021/061929" (w/Written Opinion), :pp. 1-16 (Jul. 29, 2021).
Janeway, Jr, C., et al. Immunobiology: The Immune System in Health and Disease "Chapter 3: Antigen Recognition by B-cell and T-cell Receptors" Fifth edition, New York, NY-US: Garland Publishing,:93-104 (2001).
Jordan, G., et al., "3-(4-Hydroxyphenyl)propionic acid: the forgotten detection substrate for ligand-binding assay-based bioanalysis" Bioanalysis 9(4):407-418 (Jan. 20, 2017).
Kavita, U., et al., "A systematic study of the effect of low pH acid treatment on anti-drug antibodies specific for a domain antibody therapeutic: Impact on drug tolerance, assay sensitivity and post-validation method assessment of ADA in clinical serum samples" J Immunol Methods 448:91-104 (Sep. 1, 2017).
Kelley, M., et al., "Theoretical considerations and practical approaches to address the effect of anti-drug antibody (ADA) on quantification of biotherapeutics in circulation" AAPS J 15(3):646-658 (Jul. 1, 2013).
Moxness, M., et al., "Immunogenicity Testing by Electrochemiluminescent Detection for Antibodies Directed against Therapeutic Human Monoclonal Antibodies" Clin Chem—Oxford (Abstracts of Oak Ridge Posters), 51(10):1983-1985 (Sep. 1, 2005).
Nath, N., et al., "Development of NanoLuc bridging immunoassay for detection of anti-drug antibodies" J Immunol Methods 450:17-26 (Nov. 1, 2017).
Patton, A., et al., "An acid dissociation bridging ELISA for detection of antibodies directed against therapeutic proteins in the presence of antigen" J Immunol Methods 304(1-2):189-195 (Sep. 1, 2005).
Sawyer, W., et al., "The Dissociation of Proteins by Chaotropic Salts" J Biol Chem 248(24):8429-8433 (Dec. 25, 1973).
Shankar, G., et al., "Recommendations for the validation of immunoassays used for detection of host antibodies against biotechnology products" J Pharm Biomed Anal 48(5):1267-1281 (Dec. 15, 2008).
Sickert, D., et al., "Improvement of drug tolerance in immunogenicity testing by acid treatment on Biacore" J Immunol Method 334(1-2):29-36 (Feb. 14, 2008).
Smith, H., et al., "Detection of antibodies against therapeutic proteins in the presence of residual therapeutic protein using a solid-phase extraction with acid dissociation (SPEAD) sample treatment prior to ELISA" Regul Toxicol Pharmacol 49(3):230-237 (Dec. 1, 2007).
Thermo Fisher, Inc. et al., "Optimize elution conditions for immunoaffinity purification" Tech Tip No. 27 (Product Spec Sheet: TR0027.1),:1-2 (2009) https://assets.fishersci.com/TFS-Assets/LSG/Application-Notes/TR0027-Elution-conditions.pdf.
Tsang, V., et al., "Optimum dissociating condition for immunoaffinity and preferential isolation of antibodies with high specific activity" J Immunol Methods 138(2):291-299 (Apr. 25, 1991).
US Food & Drug Administration—FDA et al., "Immunogenicity Testing of Therapeutic Protein Products—Developing and Validating Assays for Anti-Drug Antibody Detection" Center for Biologics Evaluation and Research & Center for Drug Evaluation and Research (FDA Docket No. FDA-2009-D-0539),:1-37 (Mar. 15, 2019).
Vlasak, J., et al., "Identification and characterization of asparagine deamidation in the light chain CDR1 of a humanized IgG1 antibody" Anal Biochem 392(2):145-154 (Sep. 15, 2009).
White, J., et al., "Understanding and mitigating impact of immunogenicity on pharmacokinetic assays" Bioanalysis 3(16):1799-1803 (Aug. 30, 2011).
Xu, R., et al., "Application of an ELISA-elution assay to dissociate digoxin-antibody complexes in immunoaffinity chromatography" Scand J Immunol 71(1):55-60 (Jan. 1, 2010).
Zhong, Z.D., et al., "Drug Target Interference in Immunogenicity Assays: Recommendations and Mitigation Strategies" AAPS J 19(6):1564-1575 (Nov. 1, 2017).
Zoghbi, J., et al., "A breakthrough novel method to resolve the drug and target interference problem in immunogenicity assays" J Immunol Methods 426:62-69 (Nov. 1, 2015).

* cited by examiner

+0 µg/mL mAb1
+1 µg/mL mAb1
+500 µg/mL mAb1
over-night incubation
MgCl2 treatment
SB
Cut point (1.08)
0.1
1
10
100
10
100
1000
5000
PC1 serum concentration [ng/mL]
PC1 serum concentration [ng/mL]

over-night incubation
acid treatment
MgCl$_2$ treatment
S/B
Cut point (1.08)
0.1
1
10
100
10
100
1000
5000
PC2 plasma concentration [ng/mL]
+0 µg/mL mAb2
+1 µg/mL mAb2
+100 µg/mL mAb2

HIGH IONIC STRENGTH DISSOCIATION ASSAY FOR HIGH DRUG TOLERANT TESTING

CROSS-REFERENCE TO RELATED APPLICATIONS

This application is a continuation of International Application No. PCT/EP2021/061929, filed May 6, 2021, which claims benefit of priority to European Application No. 20173599.0, filed May 8, 2020, each of which is incorporated herein by reference in its entirety.

FIELD OF INVENTION

The current invention is in the field of immunoassays, especially in the field of anti-drug antibody (ADA) assessment. In many cases ADA assessment is challenging, especially in studies that involve the administration of high doses of biotherapeutics and/or with long half-lives. In such cases, ADA assays with optimized drug tolerance are desired. The current invention is based, at least in part, on the use of a chaotropic salt, such as, e.g., $MgCl_2$ or LiCl, in a high ionic strength dissociation assays (HISDA) to attain high drug tolerance while maintaining best possible structural integrity of ADAs.

BACKGROUND OF THE INVENTION

Immunogenicity assessment of therapeutic drug candidates is an important part of the drug development process. In cases of an immune response, appropriate interpretation of immunogenicity data is required to enable a correlation with clinical outcomes. Bioanalytical methods used for immunogenicity testing provide the required information by detecting and characterizing anti-drug antibodies (ADAs).

The “gold standard” assay format is the ADA bridging assay, where ADAs are complexed with labeled drug conjugates to form signal-giving complexes. However, this format is susceptible to interference by residual drug that forms complexes with ADAs itself and therefore prevents complex formation with assay reagents. For this reason, especially in studies that involve the administration of high doses of biotherapeutics and/or biotherapeutics with long half-lives, ADA assessment may be challenged by drug interference [1]. In such cases, an ADA assay with optimized drug tolerance is desired.

To achieve high drug tolerance, many immunogenicity testing methods aim to break up the reversible, non-covalent binding interactions that hold together immune complexes formed by ADAs and drugs, e.g. antibodies. Such interactions include electrostatic forces, hydrophobic interactions, Van der Waals forces and hydrogen bonds. A majority of such interactions can be weakened by high chaotropic salt concentrations, extremes of pH or detergents [2,3].

The use of low pH acid treatment has become a common method to dissociate immune complexes to achieve higher drug tolerance. For example, Butterfield, A. M., et al. [4] compared three acid-based assay formats with respect to drug tolerance: Meso Scale Discovery® bridging assay format [5], solid-phase extraction with acid dissociation (SPEAD) [6] and affinity capture elution (ACE) [7]. Another novel method that was developed to successfully eliminate drug interference uses a combination of precipitation and acid dissociation (PandA) [8]. Numerous other acid-based methods in many different variations have been successfully developed [9,10,11].

However, the possibility of partial denaturation of antibodies/ADAs and potentially loss of binding functionality remains a limitation of such methods [12]. Regarding immunogenicity testing, such a loss of binding functionality of ADAs to assay reagents could potentially lead to false assay results by ADA underestimation.

An alternative to PH mediated complex dissociation is the use of denaturing agents like guanidine hydrochloride. This chaotropic compound was successfully used to increase assay drug tolerance in a surface plasmon resonance-based method for the detection of ADAs [13]. The use of such denaturing agents represents a powerful tool to dissociate immune complexes. However, they are generally considered as “harsh” conditions that can potentially damage protein structures [14], which again would be disadvantageous for ADA detection.

In contrast to that, non-denaturing ionic strength conditions are considered “gentle” on antibody function by causing only minimal or no changes in secondary and tertiary structures. This approach is commonly used in chromatographic methods, e.g. for gentle protein elution in the field of immunoaffinity purification. In chromatographic methods the salt magnesium chloride ($MgCl_2$) is often used due to its relatively mild properties. For example, Durkee, K. H., et al. used a buffer containing 3.5 M $MgCl_2$ and 0.05 M Tris-HCl at neutral pH for non-denaturing elution of the enzyme RVV-X from a monoclonal antibody, whereas low- or high-pH buffers led to inactivation of the enzyme [15].

In WO 2019/105916 a target interference suppressed anti-drug antibody assay is reported. Zhong, Z. D., et al., reviewed drug target interference in immunogenicity assays-recommendations and mitigation strategies (AAPS J., 19 (2017) 1564-1575). Nath, N., et al., reported the development of NanoLuc bridging immunoassay for detection of anti-drug antibodies (J. Immunol. Meth. 450 (2017) 17-26). Brady, A., et al., reported the description of a novel multiplex avidity assay for evaluating HPV antibodies (J. Immunol. Meth. 447 (2017) 31-36). Xu, R., et al., reported the application of an ELISA-elution assay to dissociate digoxin-antibody complexes in immunoaffinity chromatography—an ELISA-elution to dissociate digoxin-antibody complexes (Scan. J. Immunol. 71 (2010) 55-60). Hogben, D. N. et al., reported HB5Ag:anti-HBs immune complexes—a method for separating the constituent components and assessment of the affinity of the antibody (J. Immunol. Meth. 93 (1986) 29-36). Dandliker, W. B., et al. reported the effect of chaotropic ions on the dissociation of antigen-antibody complexes (Biochem. 6 (1967) 1460-1467).

Tsang, V. C., et al. identified a composition of 3.0 M $MgCl_2*6H_2O$, 0.075 M HEPES/NaOH and 25% ethylene glycol at pH 7.20 as a suitable dissociation buffer for their immunoaffinity system in terms of specific activity and total quantitative yield of the eluted antibody [20]. A variety of other buffers have been tested in their study, including guanidine hydrochloride, but they did not produce high specific activities, supposedly due to denaturation effects.

BRIEF SUMMARY OF THE INVENTION

The current invention is based, at least in part, on the finding that with the addition of a chaotropic salt, such as, e.g., $MgCl_2$ or LiCl, in an anti-drug antibody (ADA) assay an improved drug tolerance can be achieved. Unexpectedly, at the same time the structural integrity of ADAs present in the sample is maintained.

The current invention is based, at least in part, on the finding that by the addition of a chaotropic salt, such as, e.g., $MgCl_2$ or LiCl, in an anti-drug antibody (ADA) assay higher signal-to-blank values can be achieved with significantly shortened incubation times, e.g. when compared to overnight incubation or acid pre-treatment. Thus, the addition and use of a chaotropic salt, such as, e.g., $MgCl_2$ or LiCl, in ADA assays provides for an improvement in sensitivity, drug tolerance, as well as handling time. Additionally the addition and use of a chaotropic salt, such as, e.g., $MgCl_2$ or LiCl, provides for an alternative in cases where acid pre-treatment for the dissociation of antibody complexes is not possible or unwanted or results in the distortion of the sample.

Herein is reported:

Item 1. A method for the detection/determination of the presence of a target antibody in a sample comprising the following steps:

a) incubating the sample (or an aliquot of the sample) with a chaotropic salt at a final cation charge normality in the range of and including 1 N to 12 N/adding to the sample a chaotropic salt to a final concentration in the range of and including 1 N to 12 N and incubating the sample thereafter;

ab) optionally: removing precipitate formed in step a) from the sample but not removing the chaotropic salt;

b) adding a tracer antibody to the sample obtained in step a) (or step ab)) and incubating the sample still comprising the chaotropic salt thereafter to form a tracer antibody-target antibody-complex;

bc) optionally recovering the tracer antibody-target antibody-complex from the sample obtained in step b);

c) incubating the (isolated) tracer antibody-target antibody-complex formed in step b) (or obtained in step bc)) with a detection antibody conjugated to a detectable label to form a tracer antibody-target antibody-detection antibody complex;

cd) optionally removing excess of tracer antibody and detecting the tracer antibody-target antibody-detection antibody complex;

whereby the target antibody is detected/the presence of the target antibody is determined if a tracer antibody-target antibody-detection antibody-complex is detected in the sample obtained in step c) or optionally cd).

Item 2. The method according to item 1, wherein the chaotropic salt is a medium strength chaotropic salt, preferably with a cation between potassium and calcium in the lyotrophic series according to Hofmeister and an anion between hydrogen phosphate and nitrate in the lyotrophic series according to Hofmeister.

Item 3. The method according to any one of items 1 to 2, wherein the chaotropic salt has a cation selected from the group of cations consisting of potassium, sodium, lithium, magnesium and calcium, and an anion selected from the group of anions consisting of hydrogen) phosphate, acetate and chloride.

Item 4. The method according to any one of items 1 to 3, wherein the chaotropic salt is $MgCl_2$ or LiCl.

Item 5. The method according to any one of items 1 to 4, wherein the final cation charge normality of the chaotropic salt is in the range of 5 N to 10 N.

Item 6. The method according to any one of items 1 to 5, wherein the final cation charge normality of the chaotropic salt is about 6.5 N to 8.5 N.

Item 7. The method according to any one of items 1 to 6, wherein the incubating in steps a) and b) is between 15 min, and 180 min.

Item 8. The method according to any one of items 1 to 7, wherein the incubating in steps a) and b) is between 25 min, and 75 min.

Item 9. The method according to any one of items 1 to 8, wherein the incubating in steps a) and b) is between 30 min, and 60 min., preferably about 30 min. or about 60 min.

Item 10. The method according to any one of items 1 to 9, wherein in step b) further a capture antibody is added together with, before or after the tracer antibody but before incubating the sample.

Item 11. The method according to any one of items 1 to 10, wherein in step b) the tracer antibody is conjugated to a label.

Item 12. The method according to any one of items 10 to 11, wherein the capture antibody and the tracer antibody and the detection antibody are conjugated to different labels, whereby the label of the capture antibody does not interact with the label of the detection antibody and vice versa.

Item 13. The method according to any one of items 1 to 12, wherein the tracer antibody is conjugated to digoxigenin.

Item 14. The method according to any one of items 10 to 13, wherein the capture antibody is conjugated to biotin or avidin/streptavidin.

Item 15. The method according to any one of items 1 to 14, wherein the tracer antibody in step b) is added to a final concentration of from 0.5 μg/mL to 5 μg/mL.

Item 16. The method according to any one of items 1 to 15, wherein the tracer antibody in step b) is added to a final concentration of from 0.9 μg/mL to 2.5 μg/mL.

Item 17. The method according to any one of items 1 to 16, wherein the tracer antibody in step b) is added to a final concentration of about 1 μg/mL.

Item 18. The method according to any one of items 10 to 17, wherein the capture antibody in step b) is added to a final concentration of from 0.5 μg/mL to 5 μg/mL.

Item 19. The method according to any one of items 10 to 18, wherein the capture antibody in step b) is added to a final concentration of from 0.9 μg/mL to 2.5 μg/mL.

Item 20. The method according to any one of items 10 to 19, wherein the capture antibody in step b) is added to a final concentration of about 1 μg/mL.

Item 21. The method according to any one of items 10 to 20, wherein the capture and the tracer antibody are added to the same final concentration.

Item 22. The method according to any one of items 1 to 21, wherein the detectable label of the detection antibody is an enzyme capable of converting the colorless form of a detection agent into the colored form of the detection agent.

Item 23. The method according to any one of items 1 to 22, wherein the detection antibody specifically binds to the label of the tracer antibody and is conjugated to horseradish peroxidase and step c) of the method is:

c) incubating the isolated tracer antibody-anti-drug antibody-complexes formed in b) with a detection antibody conjugated to horseradish peroxidase and ABTS or HPPA.

Item 24. The method according to any one of items 1 to 23, wherein the presence of a tracer antibody-target antibody-detection antibody-complex is detected in the sample obtained in step c) if a signal above the threshold cut-off level/cut-point of the assay is obtained.

Item 25. The method according to any one of items 1 to 23, wherein the presence of a tracer antibody-target antibody-detection antibody-complex is detected in the sample obtained in step c) if a signal above a pre-set threshold level is obtained.

Item 26. The method according to any one of items 1 to 23, wherein the presence of a tracer antibody-target antibody-detection antibody-complex is detected in the sample obtained in step c) if a signal above the signal level pre-determined based on the non-specific background level of the assay and the responses of samples from a drug-naive subject population of interest processed in steps a) to c) is obtained.

Item 27. The method according to any one of items 1 to 23, wherein the presence of a tracer antibody-target antibody-detection antibody-complex is detected in the sample obtained in step c) if a statistically elevated signal is obtained with respect to a sample processed in steps a) to c) but free of target antibody.

Item 28. The method according to any one of items 1 to 23, wherein the presence of a tracer antibody-target antibody-detection antibody-complex is detected in the sample obtained in step c) if a signal of at least two times the signal obtained with a sample processed in steps a) to c) but free of target antibody is obtained.

Item 29. The method according to any one of items 10 to 28, wherein step c) is
- c-1) transferring the sample obtained in step b) to a solid surface comprising a capture agent immobilized thereon that can specifically bind to the capture antibody;
- c-2) incubating the sample on the solid surface;
- c-3) removing substances not bound to the solid surface by washing;
- c-4) incubating the immobilized tracer antibody-anti-drug antibody-complexes on the solid surface with a detection antibody conjugated to a detectable label;
- c-5) removing substances not bound to the solid surface immobilized tracer antibody-anti-drug antibody-complexes by washing
- c-6) detecting the immobilized detectable label of the detection antibody.

Item 30. The method according to any one of items 10 to 29, wherein the capture agent specifically binds to the label of the capture antibody.

Item 31. The method according to any one of items 10 to 30, wherein the capture agent is biotin and the capture antibody is conjugated to avidin/streptavidin, or vice versa.

Item 32. The method according to any one of items 1 to 31, wherein the detection antibody is added to a final activity of the enzyme of from 10 mU/mL to 100 mU/mL.

Item 33. The method according to any one of items 1 to 32, wherein the detection antibody is added to a final activity of the enzyme of from 15 mU/mL to 50 mU/mL.

Item 34. The method according to any one of items 1 to 33, wherein the detection antibody is added to a final activity of the enzyme of about 25 mU/mL.

Item 35. The method according to any one of items 1 to 34, wherein the tracer antibody-target antibody-complex is isolated from 10 μL to 1000 μl of the solution obtained in step b).

Item 36. The method according to any one of items 1 to 35, wherein the tracer antibody-target antibody-complex is isolated from 50 μL to 500 μl of the solution obtained in step b).

Item 37. The method according to any one of items 1 to 36, wherein the tracer antibody-target antibody-complex is isolated from 75 μL to 125 μl of the solution obtained in step b).

Item 38. The method according to any one of items 1 to 37, wherein the tracer antibody-target antibody-complex is isolated from about 100 μL of the solution obtained in step b).

Item 39. The method according to any one of items 22 to 38, wherein the final concentration of the detection agent is about 20 mM.

Item 40. The method according to any one of items 1 to 39, wherein all method steps are performed at room temperature.

Item 41. The method according to any one of items 1 to 40, wherein the target antibody is an anti-drug antibody or a therapeutic antibody.

Item 42. The method according to any one of items 1 to 41, wherein no acid treatment/acid dissociation step is made in the method.

Item 43. The method according to any one of items 1 to 42, wherein the method is an immunoassay.

Item 44. The method according to any one of items 1 to 43, wherein the method is an enzyme-linked immunosorbent assay (ELISA).

Left: Signal-to-blank (SB) values of samples spiked with different quantities of pAb<mAb-1>Rb (PC1) tested in three variants of the mAb-1-based ADA assay (over-night incubation, $MgCl_2$ addition according to the current invention and acid treatment) plotted against PC1 serum concentration. Right: All SB values were normalized to SB values of samples treated with over-night incubation and plotted against PC1 serum concentration to assess potential signal inhibition greater than 20%.

Figure 3:
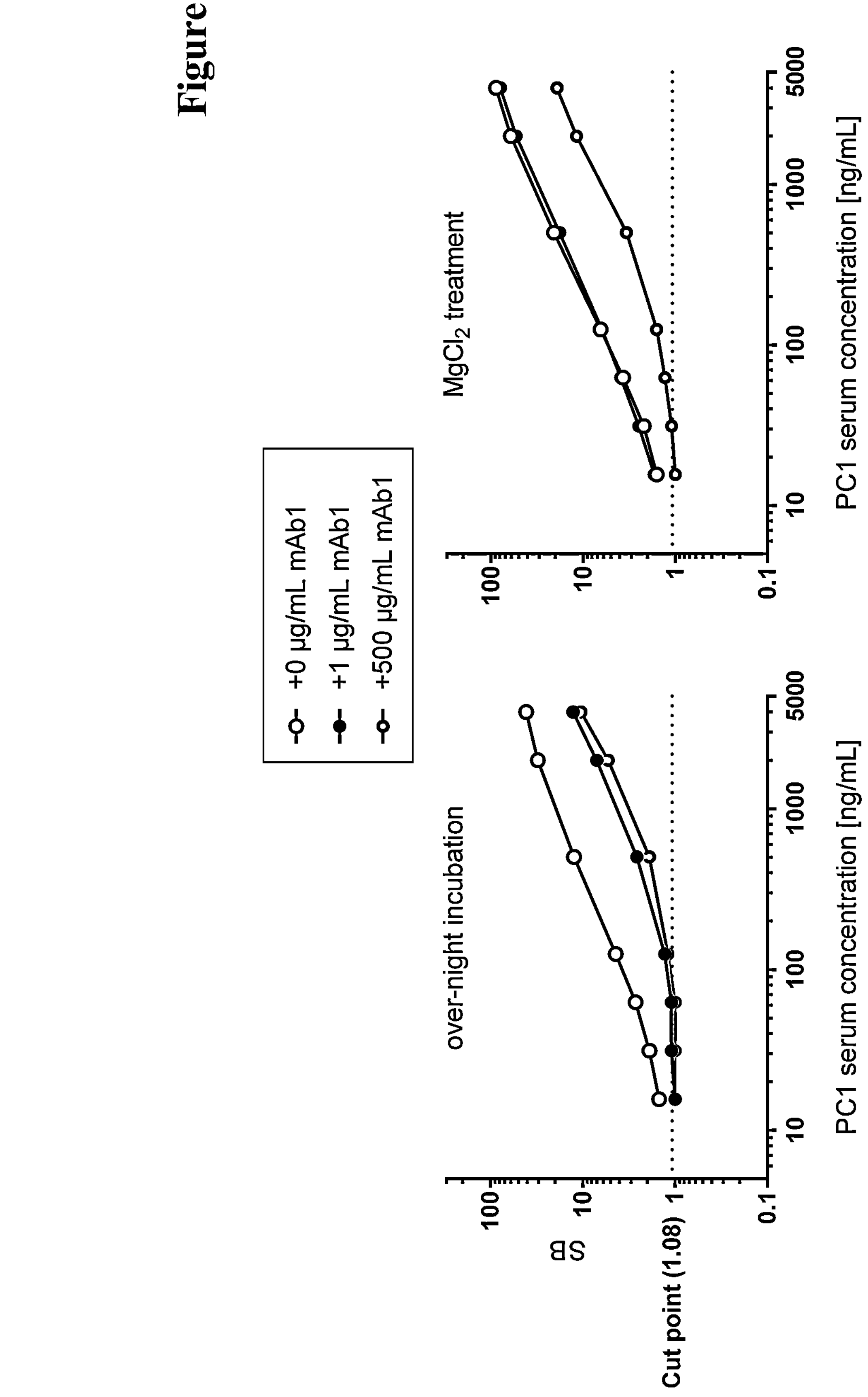

FIG. 3 Drug tolerance evaluation.

Samples spiked with different quantities of pAb<mAb-1>Rb (PC1) and mAb-1 were analyzed using two variants of the mAb-1-based ADA assay: over-night incubation (left) and $MgCl_2$ addition according to the current invention (right). Corresponding signal-to-blank (SB) values were plotted against PC1 serum concentration and compared to the cut point to assess assay drug tolerance.

Figure 4:
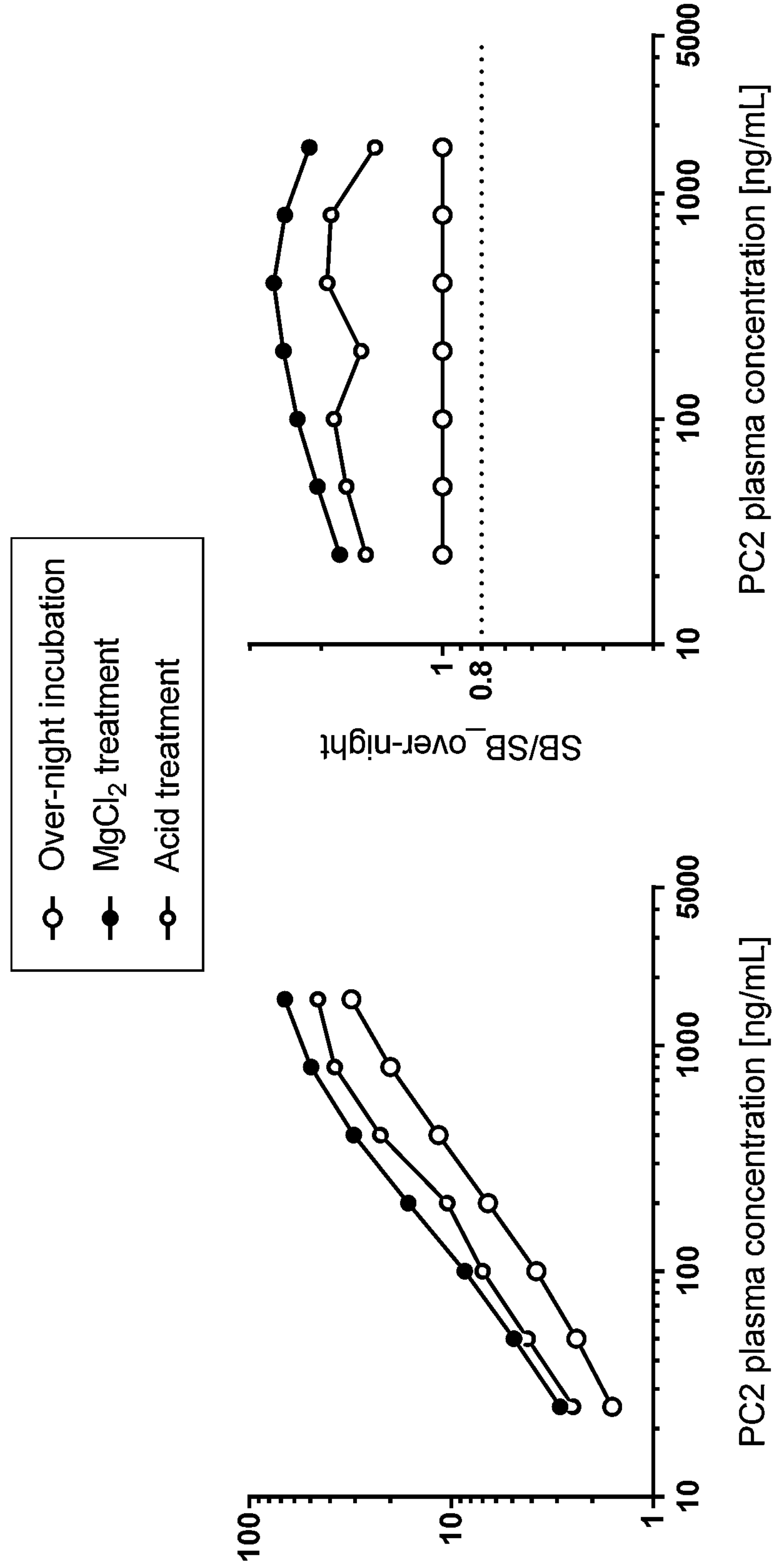

FIG. 4 Comparison of assay variants.

Left: Signal-to-blank (SB) values of samples spiked with different quantities of mAb<mAb-2>M (PC2) tested in three variants of the mAb-2-based ADA assay (over-night incubation, $MgCl_2$ addition according to the current invention and acid treatment) plotted against PC2 plasma concentration. Right: All SB values were normalized to SB values of samples treated with over-night incubation and plotted against PC2 plasma concentration to assess potential signal inhibition greater than 20%.

Figure 5:
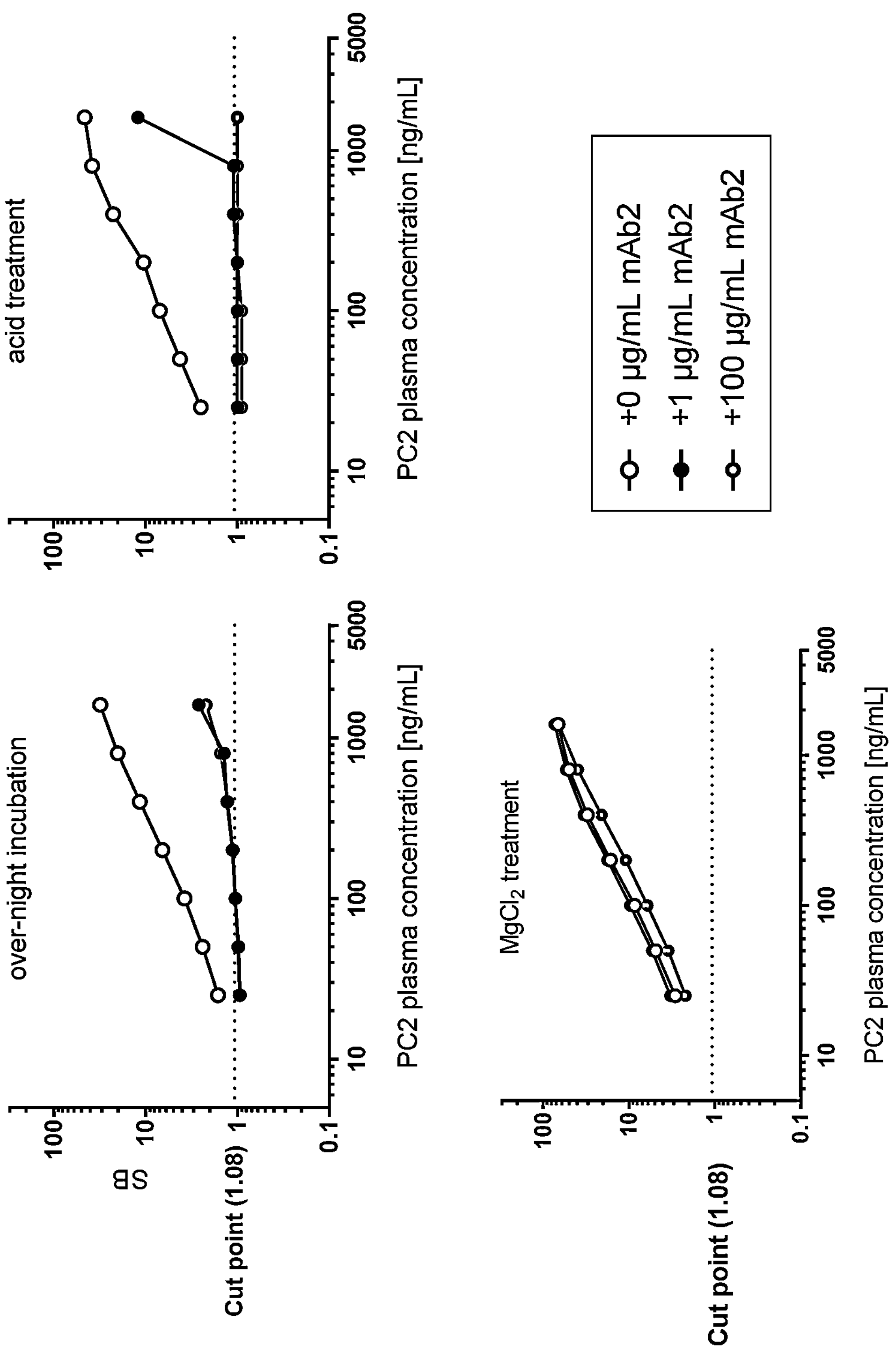

FIG. 5 Drug tolerance evaluation.

Samples spiked with different quantities of mAb<mAb-2>M (PC2) and mAb-2 were analyzed using three variants of the mAb-2-based ADA assay: over-night incubation (left), acid treatment (middle) and $MgCl_2$ addition according to the current invention (right). Corresponding signal-to-blank (SB) values were plotted against PC2 plasma concentration and compared to the cut point to assess assay drug tolerance.

Figure 6:
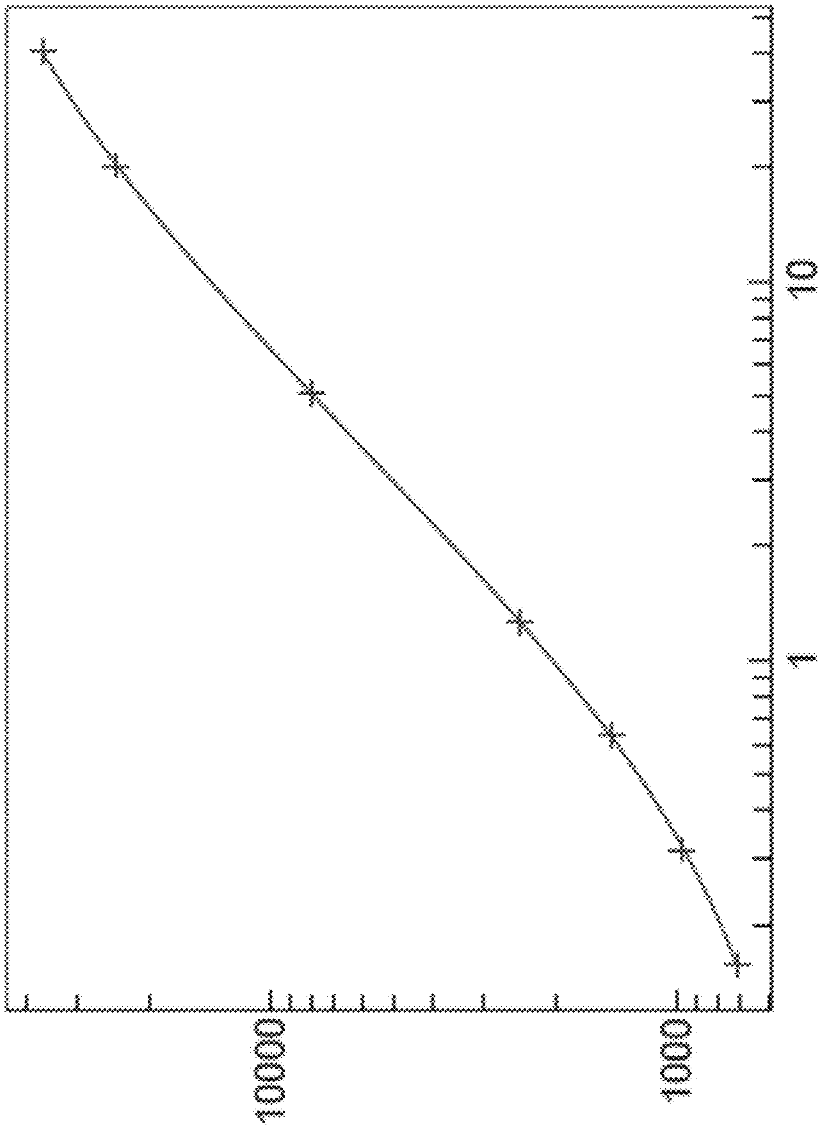

FIG. 6 A typical calibration curve for the method according to the current invention.

DETAILED DESCRIPTION OF THE INVENTION

Many different assay formats and methods have been used to address interference by residual therapeutic antibody, i.e. drug, in anti-drug antibody (ADA) assays. Especially methods that use acid steps to dissociate ADA-drug immune complexes are commonly used to improve assay drug tolerance [4,8,10,11]. A common disadvantage of these methods is that assay conditions such as pH and exposure time of acid treatment need to be carefully optimized to achieve a balance between removal of drug interference and potential antibody denaturation.

It has now been found that that with the addition of a chaotropic salt, such as, e.g., $MgCl_2$ or LiCl, in an anti-drug antibody (ADA) assay an improved drug tolerance can be achieved. Unexpectedly, at the same time the structural integrity of ADAs present in the sample is maintained.

It has further been found that by the addition of a chaotropic salt, such as, e.g., $MgCl_2$ or LiCl, in an anti-drug antibody (ADA) assay higher signal-to-blank values can be achieved in significantly shortened incubation times, e.g. when compared to over-night incubation or acid pre-treatment.

Thus, the addition and use of a chaotropic salt, such as, e.g., $MgCl_2$ or LiCl, in ADA assays provides for an improvement in sensitivity, drug tolerance, as well as handling time. Additionally the addition and use of a chaotropic salt, such as, e.g., $MgCl_2$ or LiCl, provides for an alternative in cases where acid pre-treatment for the dissociation of drug-ADA complexes is not possible or unwanted or results in the distortion of the sample.

I. DEFINITIONS

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well known in the art. Generally, nomenclatures used in connection with, and techniques of biochemistry, enzymology, molecular, and cellular biology, microbiology, genetics and protein and nucleic acid chemistry and hybridization described herein are those well-known and commonly used in the art.

Unless otherwise defined herein the term "comprising of" shall include the term "consisting of".

The term "about" as used herein in connection with a specific value (e.g. temperature, concentration, time and others) shall refer to a variation of +/−1% of the specific value that the term "about" refers to.

The term "antibody" is used herein in the broadest sense and encompasses various antibody structures, including but not limited to monoclonal antibodies, multispecific antibodies (e.g., bispecific antibodies), and antibody fragments so long as they exhibit the desired antigen-binding activity.

An antibody in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The constant domains of an antibody heavy chain comprise the CH1-domain, the CH2-domain and the CH3-domain, whereas the light chain comprises only one constant domain, CL, which can be of the kappa isotype or the lambda isotype.

The variable domain of an immunoglobulin's light or heavy chain in turn comprises different segments, i.e. four framework regions (FR) and three hypervariable regions (HVR).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, Nature Biotechnology 23:1126-1136 (2005).

The term "capture antibody" denotes an antibody that is used in a sandwich ELISA format to bind (i.e., capture) a target substance present in a sample for detection. A second antibody (i.e., the detection antibody) then binds to the captured target and allows detection of the antibody-target-antibody-complex (forming a "sandwich" comprised of antibody-target-antibody).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. In certain aspects, the antibody is of the $IgG_1$ isotype. In certain aspects, the antibody is of the $IgG_1$ isotype with the P329G, L234A and L235A mutation to reduce Fc-region effector function. In other aspects, the antibody is of the $IgG_2$ isotype. In certain aspects, the antibody is of the $IgG_4$ isotype with the S228P mutation in the hinge region to improve stability of $IgG_4$ antibody. The heavy chain constant domains that correspond to the different classes of immunoglobulins are called α, δ, ε, γ, and μ, respectively. The light chain of an antibody may be assigned to one of two types, called kappa (κ) and lambda (λ), based on the amino acid sequence of its constant domain.

A "conjugate" is fusion protein of the present invention conjugated to one or more heterologous molecule(s), including but not limited to a label, neurological disorder drug or cytotoxic agent.

The term "detection antibody" denotes an antibody, which carries a means for visualization or quantitation. Such a means is typically an enzyme (catalyzing a colored or fluorescent reaction product following the addition of a suitable substrate), such as, e.g., horseradish peroxidase, urease, alkaline phosphatase, glucoamylase and β-galactosidase. In some embodiments, the detection antibody is directed against the antigen of interest. In some embodiments, the detection antibody is an anti-species antibody. In some embodiments, the detection antibody is conjugated to a detectable label such as biotin, a fluorescent marker, or a radioisotope, and is detected and/or quantitated using this label.

The term "detection reagent" denotes a reagent, which permits the detection and/or quantitation of an antibody, bound to an antigen. In some embodiments, the detection reagent is a colorimetric substrate for an enzyme that has been conjugated to an antibody. Addition of a suitable substrate to the antibody-enzyme conjugate results in the production of a colorimetric or fluorimetric signal (e.g., following the binding of the conjugated antibody to the antigen of interest). This definition also encompasses the use of biotin and avidin-based compounds (e.g., including but not limited to neutravidin and streptavidin) as part of the detection system.

The term "ELISA" denotes an enzyme-linked immunosorbent assay. Different ELISA formats and applications are known in the art (see, e.g., Crowther, "Enzyme-Linked Immunosorbent Assay (ELISA)," in Molecular Biomethods Handbook, Rapley et al. [eds.], pp. 595-617, Humana Press, Inc., Totowa, NJ (1998); Harlow and Lane (eds.), Antibodies: A Laboratory Manual, Cold Spring Harbor Laboratory Press (1988); Ausubel et al. (eds.), Current Protocols in Molecular Biology, Ch. 11, John Wiley & Sons, Inc., New York (1994)).

One specific ELISA format is a so-called "direct ELISA". In this ELISA format a target, e.g. a polypeptide, present in a sample is detected. In a direct ELISA the sample containing the target is brought in contact with a solid phase, such as e.g., stationary or immobilized support (e.g., a microtiter plate well). The target, if present in the sample, becomes immobilized to the solid phase, and is thereafter detected directly using an enzyme-conjugated detection molecule. If the target is an antigen the detection molecule is an antibody specific for the antigen, or if the target is an antibody specific for an antigen the detection molecule is an enzyme-conjugated antibody specific for the antigen.

Another specific ELISA format is a so-called "indirect ELISA". In this ELISA format an antigen (or an antibody) is immobilized to a solid phase (e.g., a microtiter plate well). Thereafter an antigen-specific antibody (or antigen) is added followed by the addition of a detection antibody specific for the antibody that specifically binds the antigen. This detection antibody can be a "species-specific" antibody (e.g., a goat anti-rabbit antibody).

Another specific ELISA format is a so-called "sandwich ELISA". In this format the antigen is immobilized on a solid phase (e.g., a microtiter plate well) via capture by an antibody specifically binding to the antigen (i.e., a capture antibody), which is (covalently or via a specific binding pair) immobilized on the solid phase. Generally, a sample comprising the antigen is added to the solid phase, followed by washing. If the antigen of interest is present in the sample, it is bound by the capture antibody to the solid phase.

The above-specified ELISA formats can be combined. A sandwich ELISA can be a "direct sandwich ELISA", wherein the captured antigen is detected directly by using an enzyme-conjugated antibody directed against the antigen. A sandwich ELISA can be an "indirect sandwich ELISA", wherein the captured antigen is detected indirectly by using an antibody directed against the antigen, which is then detected by another enzyme-conjugated antibody which binds the antigen-specific antibody either directly or via an attached label. With a reporter reagent, the third antibody is detected.

"Framework" or "FR" refers to variable domain residues other than complementary determining regions (CDRs). The FR of a variable domain generally consists of four FR domains: FR1, FR2, FR3, and FR4. Accordingly, the CDR and FR sequences generally appear in the following sequence in VH (or VL): FR1-CDR-H1(CDR-L1)-FR2-CDR-H2 (CDR-L2)-FR3-CDR-H3 (CDR-L3)-FR4.

The terms "full length antibody", "intact antibody", and "whole antibody" are used herein interchangeably to refer to an antibody having a structure substantially similar to a native antibody structure or having heavy chains that contain an Fc region as defined herein.

A "human antibody" is one, which possesses an amino acid sequence, which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "in-vitro" denotes either an artificial environment as such or that a process or reaction is performed within such an artificial environment.

The term "in-vivo" denotes the natural environment (e.g., an animal or a cell) of a compound or that a process or reaction is performed within its natural environment.

The term "immunoassay" denotes any technique that utilizes specifically binding molecules, such as antibodies, to capture and/or detect a specific target for qualitative or quantitative analysis. In general, an immunoassay is characterized by the following steps: 1) immobilization or capture of the analyte and 2) detection and measuring the analyte. The analyte can be captured, i.e. bound, on any solid surface, such as e.g. a membrane, plastic plate, or some other solid surface.

The term "linker" denotes a chemical linker or a single chain peptidic linker that covalently connects different entities of the blood-brain-barrier shuttle module and/or the fusion polypeptide and/or the conjugate as reported herein. The linker connects for example the brain effector entity to the monovalent binding entity. For example, if the monovalent binding entity comprises a CH2-CH3 Ig entity and a scFab directed to the blood-brain-barrier-receptor, then the linker conjugates the scFab to the C-terminal end of the CH3-CH2 Ig entity. The linker conjugating the brain effector entity to the monovalent binding entity (first linker) and the linker connecting the scFab to the C-terminal end of the CH2-CH3 Ig domain (second linker) can be the same or different.

Single chain peptidic linkers, comprising of from one to twenty amino acid residues joined by peptide bonds, can be used. In certain embodiments, the amino acids are selected from the twenty naturally occurring amino acids. In certain other embodiments, one or more of the amino acids are selected from glycine, alanine, proline, asparagine, glutamine and lysine. In other embodiments, the linker is a chemical linker. In certain embodiments, the linker is a single chain peptidic linker with an amino acid sequence with a length of at least 25 amino acid residues, in one preferred embodiment with a length of 32 to 50 amino acid residues. In one embodiment the peptidic linker is a (G×S)n linker with G=glycine, S=serine, (x=3, n=8, 9 or 10) or (x=4 and n=6, 7 or 8), in one embodiment with x=4, n=6 or 7, in one preferred embodiment with x=4, n=7.

Conjugation may be performed using a variety of chemical linkers. For example, the monovalent binding entity or the fusion polypeptide and the brain effector entity may be conjugated using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). The linker may be a "cleavable linker" facilitating release of the effector entity upon delivery to the brain. For example, an acid-labile linker, peptidase-sensitive linker, photolabile linker, dimethyl linker or disulfide-containing linker (Chari et al, Cancer Res. 52 (1992) 127-131; U.S. Pat. No. 5,208,020) may be used.

Covalent conjugation can be either direct or via a linker. In certain embodiments, direct conjugation is by construction of a polypeptide fusion (i.e. by genetic fusion of the two genes encoding the monovalent binding entity towards the BBBR and effector entity and expressed as a single polypeptide (chain)). In certain embodiments, direct conjugation is by formation of a covalent bond between a reactive group on one of the two portions of the monovalent binding entity against the BBBR and a corresponding group or acceptor on the brain effector entity. In certain embodiments, direct conjugation is by modification (i.e. genetic modification) of one of the two molecules to be conjugated to include a reactive group (as non-limiting examples, a sulfhydryl group or a carboxyl group) that forms a covalent attachment to the other molecule to be conjugated under appropriate conditions. As one non-limiting example, a molecule (i.e. an amino acid) with a desired reactive group (i.e. a cysteine residue) may be introduced into, e.g., the monovalent binding entity towards the BBBR antibody and a disulfide bond formed with the neurological therapeutic antibody. Methods for covalent conjugation of nucleic acids to proteins are also known in the art (i.e., photocrosslinking, see, e.g., Zatsepin et al. Russ. Chem. Rev. 74 (2005) 77-95). Conjugation may also be performed using a variety of linkers. For example, a monovalent binding entity and a effector entity may be conjugated using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptidic linkers, comprised of from one to twenty amino acid residues joined by peptide bonds, may also be used. In certain such embodiments, the amino acid residues are selected from the twenty naturally occurring amino acids. In certain other such embodiments, one or more of the amino acid residues are selected from glycine, alanine, proline, asparagine, glutamine and lysine. The linker may be a "cleavable linker" facilitating release of the effector entity upon delivery to the brain. For example, an acid-labile linker, peptidase-sensitive linker, photolabile linker, dimethyl linker or disulfide-containing linker (Chari et al, Cancer Res. 52 (1992) 127-131; U.S. Pat. No. 5,208,020) may be used.

The term "lyotrophic series according to Hofmeister" denotes the ranking of anions and cations based on their chaotropic properties as first described by Hofmeister (Arch. Path. Anatom. Pathobiol. 24 (1888) 247-260). This lyotrophic series is for anions as follows:

$$F^- \approx SO_4^{2-} < HPO_4^{2-} < CH_3COO^- < Cl^- < NO_3^- < Br^- < ClO_3^- < I^- < ClO_4^- < SCN^- < Cl_3CCOO^-$$

and for cations as follows:

$$NH_4^+ < K^+ < Na^+ < Li^+ < Mg^{2+} < Ca^{2+} < \text{guanidinium}.$$

The chaotropic properties of the respective ion and likewise of salts containing said ion increases from the left to the right. The ions presented more to the left are denoted as anti-chaotropic or cosmotropic ions. These have precipitating properties, i.e. result in the precipitation of proteins from solutions. The ions presented more to the right are denoted as chaotropic ions. These have denaturing properties, i.e. result in the denaturation of proteins in solution.

The term "monoclonal antibody" as used herein refers to an antibody obtained from a population of substantially homogeneous antibodies, i.e., the individual antibodies comprising the population are identical, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "normality" denotes the measure of concentration equal to the gram equivalent weight of solute per liter of solution. The normality formula of interest is N=M*n, with n=the number of equivalents/the number of single-charge ions the species can react with. To convert normality to molarity or vice-versa in the case of $MgCl_2$, it has to be taken into account a 1 M solution will generate a 2 M solution of chloride ions and a 1 M solution of $Mg^{2+}$ ions, which because of their charge also have a value of 2 for n. Thus, in this case, N=(1 M)(2)=2 N, i.e. $MgCl_2$ has a cation charge normality of 2 N.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three complementary determining regions (CDRs). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively.

The term "hypervariable region" or "HVR" as used herein refers to each of the regions of an antibody variable domain which are hypervariable in sequence and which determine antigen binding specificity, for example "complementarity determining regions" ("CDRs"). These regions form the paratope or binding site.

Generally, antibodies comprise six antigen binding specificity determining regions: three in the VH (H1, H2, H3), and three in the VL (L1, L2, L3). Exemplary antigen binding specificity determining regions herein include:

(a) hypervariable loops (HVRs) occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) complementary determining regions (CDRs) occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(a+b) HVRs combined with CDRs occurring at amino acid residues 24-34 (L1), 50-56 (L2), 89-97 (L3), 26-35 (H1), 50-65 (H2), and 95-102 (H3) (Chothia and Lesk, J. Mol. Biol. 196:901-917 (1987)+Kabat et al., Sequences of Proteins of Immunological Interest, 5th Ed. Public Health Service, National Institutes of Health, Bethesda, MD (1991));

and (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262:732-745 (1996)).

Unless otherwise indicated, the HVRs are determined according to Kabat et al., supra. One of skill in the art will understand that the antigen binding specificity determining regions designations can also be determined according to Chothia, supra, McCallum, supra, or any other scientifically accepted nomenclature system.

The term "signal" as used herein encompasses any detectable physical change that can be used to indicate that a reaction has taken place, for example, binding of an antibody to its antigen. It is contemplated that signals in the form of fluorimetric or colorimetric products/reagents are specific forms of a signal and can be used in the method according to the current invention. In some embodiments of the present invention, the signal is assessed quantitatively.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly(methyl methacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

The terms "therapeutic (monoclonal) antibody" and "drug" are used interchangeably herein. These terms are used in the broadest sense and encompasses various antibody structures, including but not limited to monoclonal antibodies, polyclonal antibodies, and antibody fragments so long as they exhibit the desired antigen-binding activity.

The term "sample" as used herein denotes any biological matrix from which the determination of an ADA response can be made. Exemplary, but not limiting samples, are serum, plasma, aqueous humor, vitreous humor, retina tissue lysate, and tumor tissues. In one preferred embodiment, the sample is blood plasma.

The term "anti-drug antibody" as used herein denotes an antibody produced by the innate immune system of the recipient of a therapeutic antibody against said therapeutic antibody after administration thereof.

The term "immunogenicity" as used herein denotes the potential of a therapeutic antibody to induce an immune response in humans or animals. During drug development, immunogenicity is assessed primarily by the measurement of binding and neutralizing anti-drug antibodies.

II. SPECIFIC COMPOSITIONS AND METHODS ACCORDING TO THE INVENTION

Herein are provided methods for detecting antibodies, especially anti-drug antibodies (ADA), in a serum or plasma sample with the focus on high sensitivity and drug tolerance (drug tolerance describes the ability of an assay to analyze ADA in the presence of residual drug) (ADA screening assay).

The assay according to the current invention differs from those know in the art in the assay setup, i.e. the formation of the complex comprising the target antibody and the tracer antibody is in the presence of the same chaotropic salt that had been used to dissociate immunecomplex in the sample to be analyzed. This results in increased reactivity and thereby sensitivity of the assay according to the invention.

In the method according to the invention an in solution formation and detection of complexes of ADA and tracer antibody is employed. Tracer antibody incubation is performed simultaneously with the ADA, whereby complexes of ADA with residual drug (in case of patient samples with patient still undergoing drug treatment) were previously dissociated by using a chaotropic salt.

The methods described in the art have a significant drawback when applying these method to clinical samples in which residual therapeutic drug is circulating. High concentrations of residual drug are very often present in the samples, e.g. in case chronic diseases are treated and a therapeutic drug level is established. In these cases anti-drug antibodies are bound to circulating therapeutic drug. Thereby, in case of circulation drug the ADA epitopes are masked by the circulating drug (forming, e.g., dimer complexes) and the tracer drug cannot form complexes with the ADA. These complexed ADA of the sample are, thus, not available for detection as only free ADA could be detected.

The ability of an assay to detect ADA in the presence of residual drug is known as drug tolerance.

One aspect of the current invention is a robust and high throughput compatible high ionic strength dissociation assay (HISDA)/method wherein $MgCl_2$ is used as non-denaturing ionic strength conditioning agent to attain high drug tolerance in the assay. It has been shown in two case studies that the method according to the current invention is effective in improving drug tolerance without negative influence on assay reagents.

Thus, the HISDA method according to the invention provides a sensitive, drug tolerant and easy-to-use procedure, which can be used to improve drug tolerance in any assay.

One aspect according to the invention is a method for the determination of the presence of anti-drug antibodies in a sample comprising the following steps:

a) incubating the sample (or an aliquot of the sample) with $MgCl_2$ or LiCl at a final concentration in the range of 1 M to 6 M/adding to the sample $MgCl_2$ to a final concentration in the range of 1 M to 6 M and incubating the sample thereafter;

b) adding a tracer antibody to the sample obtained in step a) and incubating the sample thereafter;

c) incubating the isolated tracer antibody-anti-drug antibody-complexes formed in b) with a detection antibody conjugated to a detectable label, whereby the presence of an anti-drug antibody is determined if a tracer antibody-anti-drug antibody-detection antibody complex is detected in the sample obtained in step c).

In the first step of sample analysis, all samples are analyzed for being positive or negative for anti-drug antibodies (final dilution of 1:100). This screening assay results in a yes/no answer by means of a pre-defined cut point. The cut point should be defined to result in at most 5% false-positives.

In a second step, all positive samples are analyzed for specificity using an additional confirmation assay to sort out false-positive results of the initial screening assay.

The following is presented as an exemplification of the general method according to the current invention using $MgCl_2$ as chaotropic salt. This shall not be treated as a limitation as it is a mere exemplification. The true scope is set forth in the appended claims.

The high ionic strength dissociation assays (HISDA) according to the current invention has been evaluated with two investigational examples to attain high drug tolerance while maintaining best possible structural integrity of ADAs.

The improved drug tolerance by $MgCl_2$ treatment was shown using two investigational drug antibodies mAb-1, an anti-latent myostatin antibody, and mAb-2, an anti-human Abeta antibody (mAb-1-based and mAb-2-based ADA assay—see Examples 1 and 2, respectively). Each assay was initially compared using three different variants: over-night incubation (Example 4), acid treatment (Example 3) and $MgCl_2$ treatment (Example 1 or 2, respectively). As the over-night incubation is the generally used method without risk of antibody damage, this method was used as a “benchmark” in terms of PC stability and drug tolerance for the other two treatments.

First, the negative impact of acid versus $MgCl_2$ treatment on the quantification of PC compared to over-night incubation was evaluated. The evaluation was based on official acceptance criteria for bioanalytical methods [1,18].

Figure 1:
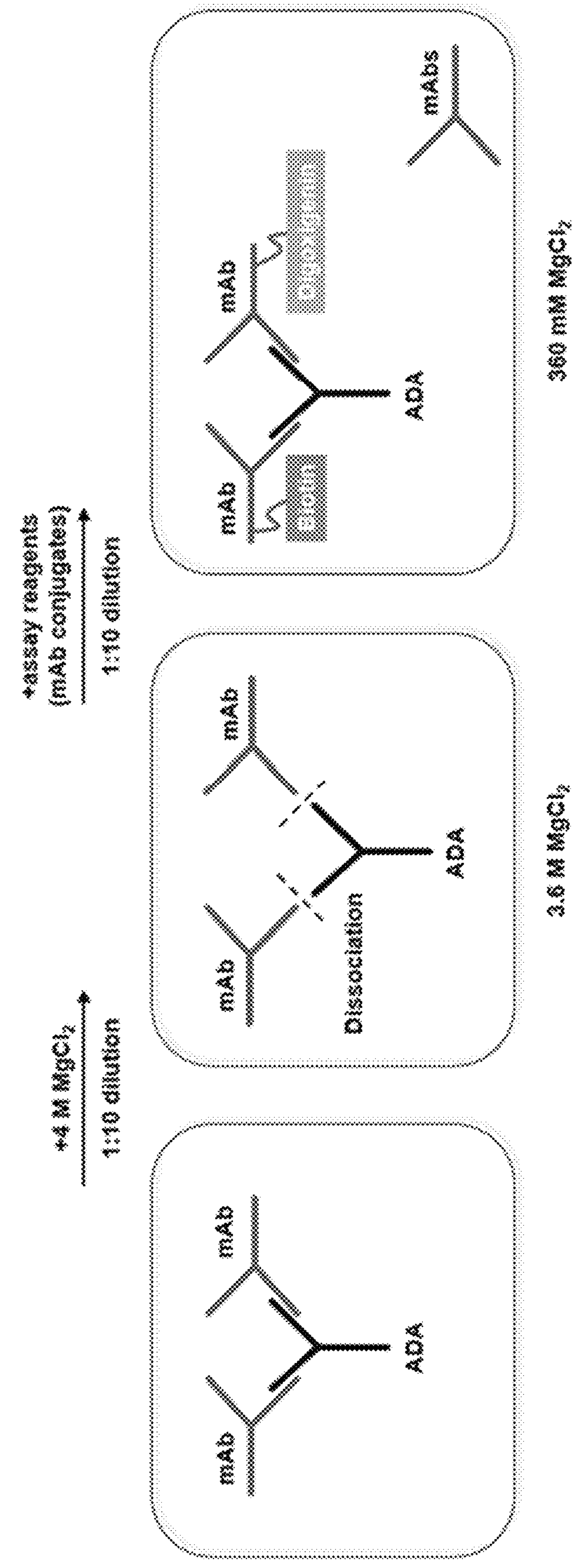
FIG. 1A 4 M $MgCl_2$*$6H_2O$ solution is added to all samples and incubated for 30 min. at room temperature to allow dissociation of potentially occurring immune complexes formed by anti-drug antibodies (ADA) and monoclonal antibodies (mAb), indicated by dashed lines. Following the initial incubation, released ADAs are complexed by the addition of labeled assay reagents (mAb-Biotin and mAb-Digoxigenin) and incubated for 30 min at room temperature. In subsequent steps, formed immune complexes are captured using a streptavidin-coated microtiter plate and detected using a horseradish peroxidase-labeled secondary antibody.
Figure 2:
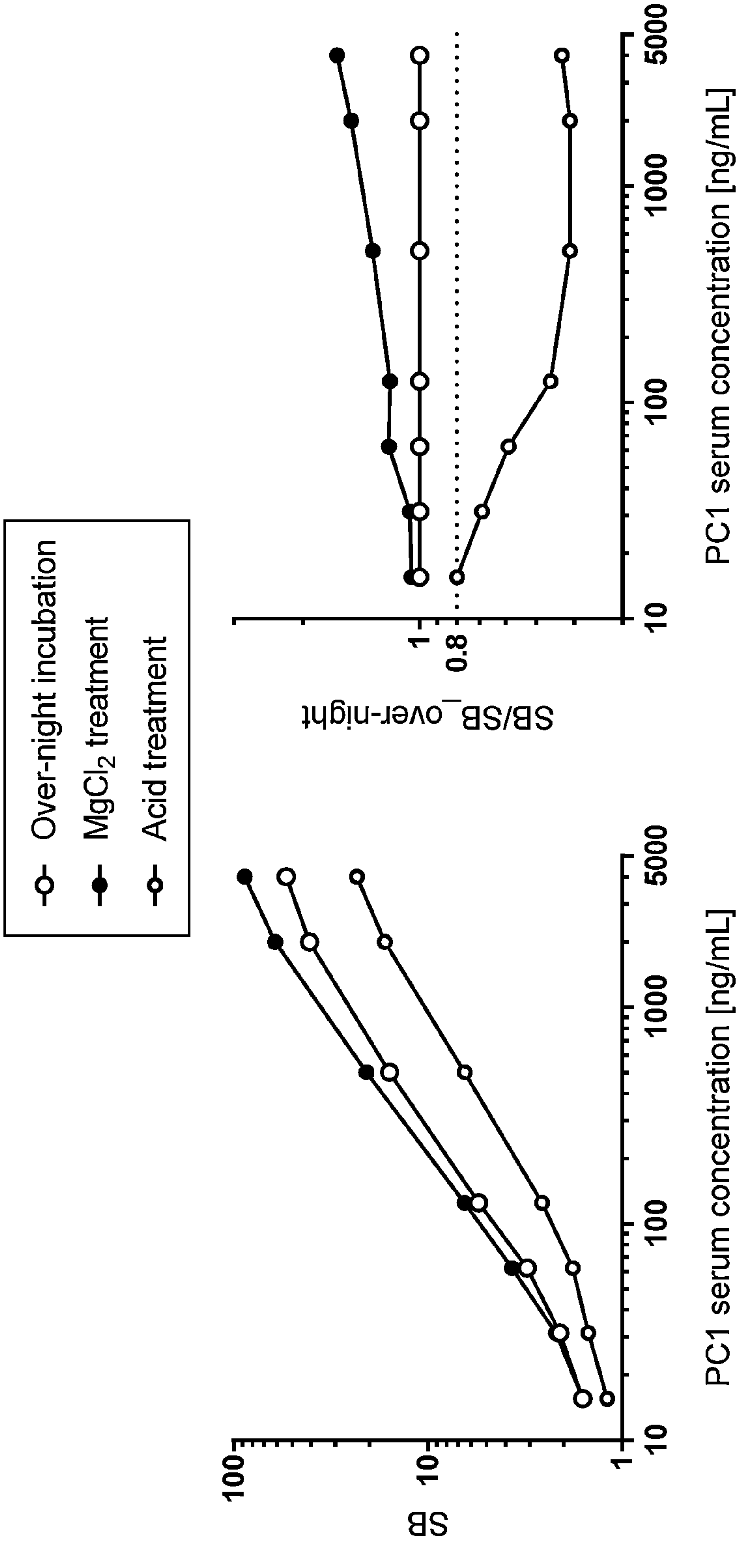
FIG. 2 Comparison of assay variants.

To allow direct comparison of the different treatments, signal-to-blank (SB) values were plotted against PC1 serum concentration (FIG. 2, left). In addition, all values were normalized to the benchmark “over-night incubation” and plotted against PC1 serum concentration to assess potential signal inhibition greater than 20% (FIG. 2, right).

As seen in FIG. 2 (right), samples treated with acid generated SB values significantly lower compared to samples treated with over-night incubation or $MgCl_2$. This observation indicated negative impact of low pH treatment on PC1 quantification. Without being bound by this theory, this is possibly due to denaturation of PC1 and/or assay reagents (mAb-1-Biotin/mAb-1-Digoxigenin). Compared with the acid treatment showed the $MgCl_2$ addition according to the method according to the current invention a higher dynamic range while having the same SB at low PC1 concentration as the over-night approach.

Thus, by omitting the necessity for acid treatment by using the method according to the current invention multiple advantages are gained. First, time-consuming evaluation work, such as, scouting of pH and exposure time to find conditions that are less harsh on critical assay components is no longer necessary. Secondly, the risk that such optimized acid treatment conditions using an artificial PC are not transferable to human ADAs [10], which is seen as a major limitation of this approach, is no longer present. Thirdly, the risk of target dimerization, causing false positive results in bridging assays [8] is no longer present. Fourthly, the risk of antibody deamidation that can have negative impact on binding potency [19] is no longer present.

Because elevated drug levels are more and more common in the clinical population, the assay drug tolerance was tested at antibody concentrations of up to 500 μg/mL serum concentration. To address this, different quantities of PC1 were tested for positivity in the presence of increasing concentrations of mAb-1 based on screening cut points (see Example 6).

Both methods exhibited a good level of sensitivity of at least 16 ng/ml PC1 serum concentration in the absence of mAb-1. At high PC1 concentrations in the absence of mAb-1, the method according to the current invention using $MgCl_2$ addition showed improved SB values (41 versus 88 at 4000 ng/mL PC1 for over-night incubation and $MgCl_2$ treatment, respectively).

Low mAb-1 serum concentrations of 1 μg/mL were generally very well tolerated over the entire PC1 concentration range in the case of the method according to the current invention using $MgCl_2$ addition. In the case of the over-night approach however, the lowest PC1 concentration (16 ng/mL) was determined to be negative, which is a false negative result.

In the presence of increasing mAb-1 levels, the method according to the invention using $MgCl_2$ addition showed improved sensitivity compared to over-night incubation. At 63 ng/mL PC1 and 500 μg/mL mAb-1, the analysis resulted in SB values of 1.03 (over-night incubation) and 1.29 ($MgCl_2$ addition).

The achieved drug tolerance (detection of 63 ng/mL PC in the presence of 500 μg/mL drug) was in a similar range compared to that of novel acid-based methods, such as PandA (detection of 14 ng/mL PC in the presence of 100 μg/mL drug) [8] but the method according to the current invention does not have the same risks as associated with the acid-based method.

The method according to the current invention using $MgCl_2$ addition reached both the sensitivity and the required drug tolerance required for assay qualification according to FDA guidelines. Thus, the method according to the current invention was successfully validated.

In a second case study using the mAb-2-based ADA assay, the different assay variants (over-night incubation, acid treatment and $MgCl_2$ treatment) were compared in a similar way based on PC2 calibration curves in absence of mAb-2 (FIG. 4).

For mAb-2 either the PC2 and/or assay reagents (mAb-2-Biotin/mAb-2-Digoxigenin) were apparently more tolerant to the acid treatment as for mAb-1 (FIG. 4, left vs. FIG. 2, left). This is not an unusual phenomenon. It has been reported that different antibodies react differently to acid treatment. Kavita, U., et al. showed that some low and intermediate affinity monoclonal antibodies were susceptible to glycine pH 2.2 treatment by losing activity in an ADA assay while others were not affected [12]. Nevertheless, the method according to the current invention still resulted in higher SB values compared to both, over-night incubation as well as acid treatment.

Compared to over-night incubation, both $MgCl_2$ addition according to the method according to the current invention and acid treatment consistently generated higher SB values over the entire PC2 concentration range. This observation can be explained by the reduction of blank values: 0.064 absorbance units (over-night incubation) were reduced to 0.028 ($MgCl_2$ addition) and 0.040 (acid treatment).

Because elevated drug levels are more and more common in the clinical population, the assay drug tolerance was tested at antibody concentrations of up to 100 μg/mL serum concentration with all three variants of the mAb-2-based ADA assay.

A high sensitivity of at least 25 ng/mL PC2 plasma concentration in the absence of mAb-2 was achieved with all three methods.

At 25 ng/mL PC2 and 100 μg/mL mAb-2, the analysis resulted in SB values of 0.94 (over-night incubation), 0.94 (acid treatment) and 2.22 ($MgCl_2$ addition). Based on the screening cut point of 1.08, the improvement by $MgCl_2$ addition was significant and even more pronounced than in the first case study.

With over-night incubation or acid treatment, it would not have been possible to reach a desired sensitivity of 100 ng/mL PC2 plasma concentration, even in the presence of low mAb-2 concentrations of 1 μg/mL, as all relevant samples were screened falsely negative. On the contrary, the same mAb-2 concentration was very well tolerated over the entire PC2 concentration range in the case of the method according to the invention using $MgCl_2$ addition.

Both the sensitivity and the required drug tolerance threshold levels were reached also in this second case study using the method according to the current invention with $MgCl_2$ addition. The method was successfully qualified thereafter.

The method according to the current invention has been used in analyzing clinical trial samples. In a study with a mAb-1-like antibody a false positive error rate (FPER) of 2.6% was determined (39 samples). In two further studies with a mAb-2-like antibody a FPER of 4.9% (366 samples) and 3.4% (354 samples), respectively, has been determined.

The above shows a further advantage of the method according to the current invention. Generally, a method for the determination of a target antibody in a sample is validated using a defined number of samples obtained from non-treated, healthy humans (a drug-naive subject population). Therewith the cut-point, i.e. the threshold for distinguishing negative from positive samples, is determined. The same is done for the clinical samples. But, if the observed FPER of the in-study clinical baseline samples, after excluding the samples with pre-existing ADA, is within the range of 2 to 11%, then the same screening assay cut-point and confirmation cut-point values determined from the pre-study validation can be applied for the clinical study sample evaluations. However, if the FPER is less than 2% or over 11%, a new study-specific SCP and CCP should be determined using the clinical study baseline samples (see, e.g., Devanarayan, V., et al., AAPS J. 19 (2017) 1487-1498). Thus, the method according to the invention showed to be robustly close or even below the target of 5%. Thereby, the need to re-do the assay development is eliminated.

Thus, it has been shown in two different case studies and clinical trials, that the addition of $MgCl_2$ can successfully be used to dissociate immune complexes formed by ADA and therapeutic drugs, resulting in improved assay drug tolerance.

Regarding complex dissociation in immunogenicity testing, it is equally important to maintain the binding activity of ADAs, otherwise the screening result could be falsified. In both case studies, no negative influence of the addition of $MgCl_2$ according to the method according to the current invention on the PC and/or assay reagents.

Due to the simplicity of the HISDA protocol according to the current invention, the method is less prone to errors compared to methods with more steps and/or where pH values and exposure times must be set accurately. The combination of a relatively small number of adjustable parameters and short incubation times also makes the method suitable for high throughput applications.

With the increasing number of therapeutic drug candidates, the demand for immunogenicity testing will continue to grow in the future. The bioanalytical methods used for immunogenicity testing are of particular importance as they are used to generate critical clinical data. Such methods must be developed in a way that they are free from technological bias such as interference from drug. The use of the method according to the current invention allows for the generation of meaningful, unequivocal data and, thus, allows for improved and robust immunogenicity testing. The HISDA method principle according to the current invention can be applied to any type of immunoassays whose performance is influenced by binding partners. This is of particular interest for bioanalytical support of pharmacokinetic evaluation of new drug candidates, when clearly defined total drug information [21] is required in the presence of relevant concentrations of soluble ligand or in the presence of anti-drug antibodies [9,22].

The following examples and figures are provided to aid the understanding of the present invention, the true scope of which is set forth in the appended claims. It is understood that modifications can be made in the procedures set forth without departing from the spirit of the invention.

REFERENCES

Reference List

1. Immunogenicity Testing of Therapeutic Protein Products—Developing and Validating Assays for Anti-Drug Antibody Detection. https://www.fda.gov (2019)
2. Janeway, C. J., et al., Antigen-antibody interactions involve a variety of forces. In: Immunobiology: The Immune System in Health and Disease. Garland Science, 3-9 (2001)
3. Sawyer, W. H. and Puckridge, J., J. Biol. Chem. 248 (1973) 8429-8433.
4. Butterfield, A. M., et al., Bioanal. 2 (2010) 1961-1969.
5. Moxness, M., et al., Clin. Chem. 51 (2005) 1983-1985.
6. Smith, H. W., et al., Regul. Toxicol. Pharmacol. 49 (2007) 230-237.
7. Bourdage, J. S., et al., J. Immunol. Meth. 327 (2007) 10-17.
8. Zoghbi, J., et al., J. Immunol. Meth. 426 (2015) 62-69.
9. Kelley, M., et al., AAPS. J. 15 (2013) 646-658.
10. Sickert, D., et al., J. Immunol. Meth. 334 (2008) 29-36.
11. Patton, A., et al., J. Immunol. Meth. 304 (2005) 189-195.
12. Kavita, U., et al., J. Immunol. Meth. 448 (2017) 91-104.
13. Barbosa, M. D., et al., Anal. Biochem. 441 (2013) 174-179.
14. Optimize elution conditions for immunoaffinity purification. http://tools.thermofisher.com/content/sfs/brochures/TR0027-Elution-conditions.pdf (2009)
15. Durkee, K. H., et al., Prot. Expr. Purif. 4 (1993) 405-411.
16. Jordan, G., et al., Bioanal. 9 (2017) 407-418.
17. Shankar, G., et al., J. Pharm. Biomed. Anal. 48 (2008) 1267-1281.
18. Guideline on bioanalytical method validation. https://www.ema.europa.eu (2012)
19. Vlasak, J., et al., Anal. Biochem. 392 (2009) 145-154.
20. Tsang, V. C. and Wilkins, P. P., J. Immunol. Meth. 138 (1991) 291-299.
21. Heinrich, J., et al. Bioanal. 7 (2015) 3057-3062.
22. White, J. T., et al., Bioanal. 3 (2011) 1799-1803.

EXAMPLES

Materials

Positive Controls

A polyclonal rabbit-derived antibody (pAb<mAb-1>Rb; Roche Diagnostics GmbH, Germany) directed against the therapeutic monoclonal mAb-1 was used as positive control (PC1) in the mAb-1-based ADA assay. It was dissolved at 2.0 mg/mL in 1× phosphate-buffered saline (PBS; Roche Diagnostics GmbH, Germany).

A monoclonal mouse-derived antibody (mAb<mAb-2>M; Roche Diagnostics GmbH, Germany) directed against the therapeutic monoclonal mAb-2 was used in the mAb-2-based ADA assay (PC2). It was dissolved at 5.4 mg/mL in an aqueous solution of 50 mM potassium phosphate (Merck Chemicals GmbH, Germany) and 150 mM potassium chloride (Merck Chemicals GmbH, Germany), pH 7.5.

Human Matrices

Human pooled sera and human pooled K3EDTA plasma, both from mixed gender, were obtained from TRINA Bioreactives AG, Switzerland.

Example 1 mAb-1-Based ADA Assay (with $MgCl_2$ Treatment) According to the Invention

For the qualitative detection of antibodies directed against the therapeutic monoclonal mAb-1, a bridging enzyme-linked immunosorbent assay (ELISA) was used.

PC1 was used to generate quality control samples in human pooled sera. Quality control samples, negative control samples and test samples were diluted 1:10 (5 μL+45 μL) using a 4 M $MgCl_2*6H_2O$ solution (VWR International bvba, Belgium) and incubated for 30 min. at room temperature with shaking at 450 rpm. Subsequently, all samples were diluted 1:10 (30 μL of the previous dilution+270 μL) using 1×PBS containing 1× Western Blocking Reagent (Merck Chemicals GmbH, Germany), together with 900 ng/ml mAb-1-Biotin and 900 ng/ml mAb-1-Digoxigenin and incubated for 30 min. at room temperature with shaking at 450 rpm). Formed immune complexes (100 μL) were transferred to a streptavidin (SA)-coated microtiter plate (MTP) and incubated for one hour at room temperature with shaking at 450 rpm to immobilize immune complexes via the Biotin-labeled capture antibody.

After three washing steps each using 300 μL 1×PBS (phosphate buffered saline) containing 0.05% (v/v) Tween 20, 100 μL of a 25 mU/mL horseradish peroxidase (HRP)-labeled anti-Digoxigenin Fab fragments (<Digoxigenin>HRP; Roche Diagnostics GmbH, Germany) diluted in 1×PBS containing 0.5% (w/v) BSA (Merck Chemicals GmbH, Germany) were added to the MTP and incubated for one hour at room temperature with shaking at 450 rpm.

After three washing steps, substrate reaction was carried out by adding 100 μL/well 20 mM 3-p-hydroxyphenyl propionic acid (HPPA; Merck Chemicals GmbH, Germany) supplemented with 0.02% (v/v) of a hydrogen peroxide solution 30% (w/w) ($H_2O_2$; Merck Chemicals GmbH, Germany), dissolved in 0.1 M tris(hydroxymethyl)aminomethane (TRIS; Merck Chemicals GmbH, Germany) solution, pH 8.5 and incubated for 10 min. at room temperature with shaking at 450 rpm [16]. Fluorescence intensity was determined using an excitation wavelength of 320 nm and an emission wavelength of 400 nm on a microplate reader (Infinite F200; Tecan, Switzerland) at optimal gain.

A typical calibration curve is shown in FIG. 6. The values are presented in the Table below.

| serum concentration [ng/mL] | 4000 | 2000 | 500 | 125 | 62.5 | 31 | 16 | blank |
|---|---|---|---|---|---|---|---|---|
| average emission [FU] | 36804 | 24250 | 8021 | 2458 | 1471 | 982 | 721 | 476 |

A sample was defined as "potentially ADA positive" if the associated signal was at or above the screening cut point value that was calculated to generate a false-positive rate of 5% based on the assumption of a coefficient of variation of 5% regarding the screening of individual donors. The assay had a sensitivity of at least 16 ng/mL PC1 in 100% human serum. Potentially ADA positive results were confirmed in a second, confirmatory assay which was identical to the screening assay with the difference that test samples were incubated with an excess of the therapeutic monoclonal mAb-1 (100 μg/mL final assay concentration) in the mAb-1-Bi and mAb-1-Dig containing buffer.

This method was developed and qualified according to recommendations [1,17] and was also successfully validated.

Example 2 mAb-2-Based ADA Assay (with $MgCl_2$ Treatment) According to the Invention

For the qualitative detection of antibodies directed against the therapeutic monoclonal mAb-2, a bridging ELISA was used.

PC2 was used to generate quality control samples in human pooled K3EDTA plasma. 5 μL of quality control samples, negative control samples and test samples were diluted with 45 μL 4 M $MgCl_2$*$6H_2O$ solution resulting in a dilution of 1:10 and incubated for 30 min at room temperature with shaking 450 rpm. Subsequently, 30 μL of all samples were diluted 1:10 using 270 μL Roche Universal Buffer (Roche Diagnostics GmbH, Germany), together with 2000 ng/ml mAb-2-Biotin and 2000 ng/ml mAb-2-Digoxigenin and incubated for 30 min. at room temperature with shaking at 450 rpm. Formed immune complexes were transferred to a SA-coated MTP (100 μL/well) and incubated for one hour at room temperature with shaking at 450 rpm.

After three washing steps each using 300 μL 1×PBS containing 0.05% (v/v) Tween 20, 25 mU/mL anti-Digoxigenin antibody-HRP conjugate diluted in Roche Universal Buffer (100 μL/well) were added to the MTP and incubated for one hour at room temperature with shaking at 450 rpm.

After three washing steps, substrate reaction was carried out by adding 100 μL/well 2,2'-azino-bis-3-ethylbenzthiazoline-6-sulphonic acid solution (ABTS; Roche Diagnostics GmbH, Germany) and optical density was measured at a wavelength of 405 nm with a reference wavelength at 490 nm on a microplate reader (Sunrise; Tecan, Switzerland) until the quality control sample containing 1600 ng/mL PC2 reached 2.0±0.1 absorbance units. The final absorbance was calculated as follows: absorbance (405 nm)-absorbance (490 nm).

A sample was defined as "potentially ADA positive" if the associated signal was at or above the screening cut point value that was calculated to generate a false-positive rate of 5% based on the assumption of a coefficient of variation of 5% regarding the screening of individual donors. The assay had a sensitivity of at least 25 ng/mL PC2 in 100% human plasma. Potentially ADA positive results were confirmed in a second, confirmatory assay which was identical to the screening assay with the difference that test samples were incubated with an excess of the therapeutic monoclonal mAb-2 (100 μg/mL final assay concentration) in the mAb-2-Bi and mAb-2-Dig containing buffer.

This method was developed and qualified according to recommendations [1,17].

Example 3—Comparative Example

Acid Treatment

Acid dissociation was performed using the mAb-1-based and mAb-2-based ADA assay according to corresponding assay protocols with the following difference to treatment with $MgCl_2$ of Examples 1 and 2:3 μl quality control samples, negative control samples and test samples were diluted with 17 μL corresponding assay buffer followed by addition of 100 μL 0.1 M Glycine-HCl pH 2.0 (Merck Chemicals GmbH, Germany) resulting in a final dilution of 1:40 and incubated for 30 min. at room temperature with shaking at 450 rpm. Subsequently, all samples were adjusted to neutral pH by 2.5-fold dilution with 0.5 M Tris-HCl pH 8.5 (Merck Chemicals GmbH, Germany) together with corresponding concentrations of Biotin- and Digoxigenin-labeled assay reagents and incubated for 30 min. (120 μL acidified sample; 30 μL labeled reagent, 150 μL 0.5 M Tris buffer) at room temperature with shaking at 450 rpm. Subsequently, formed immune complexes (100 μL/well) were transferred to a SA-coated MTP as described in the corresponding $MgCl_2$ assay protocol of Examples 1 and 2.

Example 4—Comparative Example

Over-Night Incubation

The assay variant "over-night incubation" was performed using the mAb-1-based and mAb-2-based ADA assay according to corresponding assay protocols with the following difference to treatment with $MgCl_2$ of Examples 1 and 2:3 μL quality control samples, negative control samples and test samples were diluted 1:50 using 147 μL of the corresponding assay buffer. Subsequently, all 50-fold diluted samples were further diluted 1:2 by addition of 150 μL assay buffer containing corresponding concentrations of Biotin- and Digoxigenin-labeled assay reagents and incubated over-night at room temperature with shaking at 450 rpm. The next day, formed immune complexes were transferred to a SA-coated MTP (100 μL/well) as described in the corresponding $MgCl_2$ assay protocol of Examples 1 and 2.

Example 5

Drug Tolerance

The ability to detect ADA in the presence of therapeutic drug (assay drug tolerance) was determined using the respective PC and drug in each ADA assay. Tested combinations were PC1/mAb-1 and PC2/mAb-2. PC concentrations were chosen to comply with the FDA's ADA assay sensitivity recommendation of at least 100 ng/ml [1] and drug concentrations were chosen based on the expected levels of circulating drug in study samples.

Different quantities of respective PC were added into ADA-negative human serum or plasma samples in the presence or absence of different concentrations of drug and incubated for 3 hours at room temperature with shaking at 450 rpm to allow immune complex formation. Subsequently, samples were frozen and stored over-night at −80° C. and analyzed the next day according to corresponding assay protocols. The highest concentration of drug resulting in a mean signal at or above the screening cut point was considered the assay drug tolerance for a given PC concentration.

Example 6

Determination of Screening Cut Points

According to the description provided for mAb1 (Example 1) the sensitivity of the assay was assessed by screening of 64 healthy volunteer sera samples. Signals were normalized with the corresponding sera pool value. The normalized values are presented in the Table below.

| ID | normalized signal |
|---|---|
| 1 | 1.105 |
| 2 | 1.041 |
| 3 | 1.053 |
| 4 | 1.058 |

-continued

| ID | normalized signal |
|---|---|
| 5 | 1.103 |
| 6 | 1.070 |
| 7 | 1.055 |
| 8 | 1.060 |
| 9 | 1.091 |
| 10 | 1.055 |
| 11 | 1.008 |
| 12 | 1.062 |
| 13 | 1.103 |
| 14 | 1.120 |
| 15 | 1.081 |
| 16 | 1.054 |
| 17 | 1.150 |
| 18 | 1.018 |
| 19 | 1.001 |
| 20 | 1.025 |
| 21 | 1.001 |
| 22 | 1.034 |
| 23 | 1.540 |
| 24 | 1.077 |
| 25 | 1.232 |
| 26 | 1.006 |
| 27 | 0.994 |
| 28 | 1.008 |
| 29 | 0.985 |
| 30 | 0.995 |
| 31 | 1.030 |
| 32 | 1.011 |
| 33 | 1.118 |
| 34 | 1.019 |
| 35 | 1.033 |
| 36 | 1.047 |
| 37 | 1.054 |
| 38 | 1.057 |
| 39 | 1.057 |
| 40 | 1.012 |
| 41 | 1.081 |
| 42 | 1.007 |
| 43 | 0.994 |
| 44 | 1.015 |
| 45 | 1.013 |

-continued

| ID | normalized signal |
|---|---|
| 46 | 1.010 |
| 47 | 0.994 |
| 48 | 1.050 |
| 49 | 1.170 |
| 50 | 1.007 |
| 51 | 0.978 |
| 52 | 0.985 |
| 53 | 0.977 |
| 54 | 0.965 |
| 55 | 0.977 |
| 56 | 1.019 |
| 57 | 1.115 |
| 58 | 1.015 |
| 59 | 0.995 |
| 60 | 0.982 |
| 61 | 0.966 |
| 62 | 0.982 |
| 63 | 0.999 |
| 64 | 0.980 |

Normalized values were checked for normal distribution using R (version 3.5.1 (2018-07-02) "Shapiro-Wilk normality test" and a non-normal distribution was determined. The 64 values were then analyzed using an outlier-test based on 1.5 IQR and three values were excluded (ID: 23, 25 and 49) and retested for normal distribution with p value=0.01, still non-normal distributed. Due to the non-normal distribution, the sensitivity calculation was based on the 95 quantil of the outlier removed values and was calculated to 1.115 (Excel, quantil function, Microsoft Office Standard 2016) and a back calculation (extrapolated) resulted in a sensitivity of 4.96 ng/mL PC1 in 100% serum. Calibration data is shown in following Table, based on normalized signal versus PC1 concentration.

| concentration PC1 in serum | 4000 | 2000 | 500 | 125 | 63 | 31 | 16 | 0 |
|---|---|---|---|---|---|---|---|---|
| S/B | 82.94 | 49.12 | 17.16 | 5.24 | 3.15 | 2.05 | 1.53 | 1.00 |

Example 7

Binding Disruption by the Use of LiCl and Maintaining Activity of the Analyte An antibody of 145.8 kDa molecular weight was used as analyte. The antibody is capable to bind recombinant human (rh) mesotheline either in a "one to one" or "one to two" complex. To evaluate the complex disruption properties of LiCl the antibody was incubated at different concertation with different ratios of rh-mesotheline forming in sum 50% of total free and partial free antibody based on the total used concentration of the antibody in the sample. Horse serum was used as sample matrix. These samples were analyzed by a homogenous ligand binding assay using biotinylated rh-mesotheline as capture reagent and human IgG specific detection antibody conjugated to ruthenium for signal generation. The QC samples were analyzed in two ways. Once with incubation with 8 M LiCl to disrupt the complexes and analyzing total antibody concentration and once without LiCl to analyze free antibody concentration by confirming the stability of the complexes during assay procedure.

| preparation of the QC samples | | | | | | |
|---|---|---|---|---|---|---|
| | total (with LiCl incubation) | | | free (50% to total; without LiCl incubation) | | |
| QC | target concentration | analyzed total | | target concentration | analyzed free | |
| sample | [ng/mL] | [ng/mL] | recovery | [ng/mL] | [ng/mL] | recovery |
| #1 | 200000 | 160772 | 80% | 100000 | 85081 | 85% |
| #2 | 40000 | 43508 | 109% | 20000 | 20211 | 101% |
| #3 | 10000 | 10413 | 104% | 5000 | 4637 | 93% |
| #4 | 1000 | 1074 | 107% | 500 | 559 | 112% |
| #5 | 280 | 293 | 105% | 140 | 129 | 92% |
| #6 | 100 | 110 | 110% | 50 | 53 | 105% |

The results indicate a sufficient complex disruption by maintaining the binding properties of the antibody in the investigated range of 100 to 200,000 ng/mL in serum.

The invention claimed is:

1. A method for the detection of a target antibody in a sample comprising the following steps:

a) incubating the sample with a chaotropic salt at a final cation charge normality in the range of 1 N to 12 N;

b) adding a tracer antibody to the sample obtained in step a) and incubating the sample thereafter under conditions wherein the tracer antibody binds to either to a variable region or a constant region of the target antibody, thereby forming a tracer antibody-target antibody-complex in the presence of the chaotropic salt;

c) incubating the tracer antibody-target antibody-complex formed in step b) with a detection antibody conjugated to a detectable label under conditions wherein the detection antibody binds to a variable region or a constant region of the tracer antibody in the tracer antibody-target antibody-complex, thereby forming a tracer antibody-target antibody-detection antibody complex;

whereby the target antibody is detected if a tracer antibody-target antibody-detection antibody-complex is detected in the sample obtained in step c), wherein the chaotropic salt is $MgCl_2$ or $LiCl_2$, and wherein the method is enzyme-linked immunosorbent assay (ELISA).

2. The method according to claim 1, wherein the chaotropic salt is a medium strength chaotropic salt, and wherein the medium strength chaotropic salt comprises a cation between potassium and calcium in the lyotrophic series according to Hofmeister and an anion between hydrogen phosphate and nitrate in the lyotrophic series according to Hofmeister.

3. The method according to claim 1 or claim 2, wherein the chaotropic salt has a cation selected from the group of cations consisting of potassium, sodium, lithium, magnesium and calcium, and an anion selected from the group of anions consisting of (hydrogen)phosphate, acetate and chloride.

4. The method according to claim 1, wherein the final cation charge normality of the chaotropic salt is in the range of and including 6.5 N to 8.5 N.

5. The method according to claim 1, wherein the final $MgCl_2$ cation charge normality is 7.2 N+/−10% corresponding to a final $MgCl_2$ concentration of 3.6 M+/−10% or the final LiCl cation charge normality is 8 N+/−10% corresponding to a concentration of 8 M+/−10%.

6. The method according to claim 1, wherein the incubating in steps a) and b) is between 30 min.+/−10% to 60 min.+/−10%.

7. The method according to claim 1, wherein step b) further comprises adding a capture antibody before or after the tracer antibody, but before step c).

8. The method according to claim 7, wherein the capture antibody, the tracer antibody, and the detection antibody are each conjugated to a different label, wherein the label of the capture antibody does not interact with the label of the detection antibody and vice versa.

9. The method according to claim 8, wherein step c) comprises:

c-1) transferring the sample obtained in step b) to a solid surface comprising a capture agent immobilized thereon that can specifically bind to the capture antibody;

c-2) incubating the sample on the solid surface;

c-3) removing substances not bound to the solid surface by washing;

c-4) incubating the immobilized tracer antibody-target antibody-complex on the solid surface with a detection antibody conjugated to a detectable label;

c-5) removing substances not bound to the solid surface immobilized tracer antibody-target antibody-complexes by washing; and c-6) detecting the immobilized detectable label of the detection antibody.

10. The method according to claim 7, wherein the capture antibody in step b) is added to a final concentration of from 0.9 μg/mL to 2.5 μg/mL.

11. The method according to claim 1, wherein the tracer antibody is conjugated to a label.

12. The method according to claim 11, wherein the detection antibody is conjugated to horseradish peroxidase and specifically binds to the label of the tracer antibody, and step c) of the method comprises:

c) incubating the isolated tracer antibody-target antibody-complex formed in step b) with a detection antibody conjugated to horseradish peroxidase, and with ABTS or HPPA, under conditions wherein the detection antibody specifically binds to the label of the tracer antibody.

13. The method according to claim 1, wherein the tracer antibody in step b) is added to a final concentration of from 0.9 μg/mL to 2.5 μg/mL.

14. The method according to claim 1, wherein the target antibody is an anti-drug antibody or a therapeutic antibody.

* * * * *